United States Patent [19]

Yoshida et al.

[11] Patent Number: 4,874,546
[45] Date of Patent: Oct. 17, 1989

[54] PHENYLPYRIMIDINECARBOXYLATE DERIVATIVE

[75] Inventors: Naoyuki Yoshida, Kamakura; Kisei Kitano; Tetsuya Ogawa, both of Yokohama, all of Japan

[73] Assignee: Chisso Corporation, Japan

[21] Appl. No.: 75,657

[22] Filed: Jul. 20, 1987

Related U.S. Application Data

[63] Continuation-in-part of Ser. No. 863,505, May 15, 1986, abandoned.

[30] Foreign Application Priority Data

May 15, 1985 [JP] Japan .................. 60-103512
May 21, 1985 [JP] Japan .................. 60-108504

[51] Int. Cl.$^4$ .................. G02F 1/13; C09K 19/34; C07D 239/02
[52] U.S. Cl. .................. 252/299.61; 350/350 R; 350/350 S; 544/298; 544/335
[58] Field of Search ............. 252/299.61; 350/350 R, 350/350 S; 544/335, 298

[56] References Cited

U.S. PATENT DOCUMENTS

| | | | |
|---|---|---|---|
| 4,062,798 | 12/1977 | Boller et al. .................. | 252/299 |
| 4,118,217 | 10/1978 | Oestreicher et al. ........... | 252/299.61 |
| 4,311,610 | 1/1982 | Zaschke et al. ............... | 252/299 |
| 4,358,393 | 11/1982 | Zaschke et al. ............... | 252/299.61 |
| 4,389,329 | 6/1980 | Boller et al. .................. | 252/299.61 |
| 4,521,327 | 6/1985 | Demus et al. ................. | 252/299.61 |
| 4,565,425 | 1/1986 | Petrzilka et al. .............. | 252/299.61 |
| 4,581,155 | 4/1986 | Goto et al. ................... | 252/299.61 |
| 4,623,477 | 11/1986 | Ogawa et al. ................. | 252/299.61 |
| 4,683,078 | 7/1987 | Sugimori et al. .............. | 252/299.61 |
| 4,713,197 | 12/1987 | Eidenschink et al. .......... | 252/299.61 |

FOREIGN PATENT DOCUMENTS

| | | | |
|---|---|---|---|
| 56501 | 7/1982 | European Pat. Off. ....... | 252/299.61 |
| 149238 | 7/1985 | European Pat. Off. ....... | 252/299.61 |
| 2257588 | 6/1970 | Fed. Rep. of Germany ... | 252/299.61 |
| 3205638 | 8/1983 | Fed. Rep. of Germany . | |
| 3404116 | 8/1985 | Fed. Rep. of Germany ... | 252/299.61 |
| 3411571 | 10/1985 | Fed. Rep. of Germany ... | 252/299.61 |
| 3515373 | 11/1986 | Fed. Rep. of Germany ... | 252/299.61 |
| 3515374 | 11/1986 | Fed. Rep. of Germany ... | 252/299.61 |
| 3518734 | 11/1986 | Fed. Rep. of Germany ... | 252/299.61 |
| 55-27056 | 7/1980 | Japan ........................... | 252/299.61 |
| 56-164169 | 4/1981 | Japan ........................... | 252/299.61 |
| 56-164170 | 12/1981 | Japan ........................... | 252/299.61 |
| 56-164171 | 12/1981 | Japan ........................... | 252/299.61 |
| 56164169 | 12/1981 | Japan ........................... | 252/299.61 |
| 60-78972 | 5/1985 | Japan ........................... | 252/299.61 |
| 60109569 | 6/1985 | Japan ........................... | 252/299.61 |
| 61-68467 | 4/1986 | Japan ........................... | 252/299.61 |
| 61-260067 | 11/1986 | Japan ........................... | 252/299.61 |
| 61-268673 | 11/1986 | Japan ........................... | 252/299.61 |
| 86/00067 | 1/1986 | PCT Int'l Appl. ............ | 252/299.61 |
| 2092169 | 8/1982 | United Kingdom ........... | 252/299.61 |
| 8600067 | 1/1986 | World Int. Prop. O. ....... | 252/299.61 |
| 8600087 | 1/1986 | World Int. Prop. O. ....... | 252/299.61 |
| 8606401 | 11/1986 | World Int. Prop. O. ....... | 252/299.61 |

OTHER PUBLICATIONS

Demus, D., et al., Flüssge Kristalle in Tabellen II, Veb Deutscner Verlage Fur Grundstoffimoustrie, Leipzig, pp. 375–388 (1984).

Zaschke, H., Advances in Liquid Crystal Research and Applications, Data, L., Ed., Pergamonpress, Oxford, (1980), pp. 1059–1074.

Pavluchenko, A. I., et al., Journal De Physique, Coll. C3, Suppl. No. 4, vol. 40, p. C3-1-4 (Apr. 1979).

Mikhaleva, M. A., et al., Khim. Getoerotsill. Soedin, vol. 9, pp. 1228–1235 (1986).

Mikhaleva, M. A., et al., Khim. Geterotsikl. Soedin., vol. 3, pp. 380–388 (1986).

Zaschke, "Heterocyclic Liquid Crystals", Advances in Liquid Crystal Research and Applications, Pergamon Press, 1059–1074 (1980).

*Primary Examiner*—Teddy S. Gron
*Attorney, Agent, or Firm*—Leydig, Voit & Mayer

[57] ABSTRACT

A novel phenylprimidinecarboxylate derivative which, when used as a component of liquid crystal compositions, can raise the clearing point of the mesomorphic range of the liquid crystal compositions and/or increase the dielectric anisotrophy value of the compositions, and a liquid crystal compositions containing the derivative are provided, which derivative is expressed by the formula

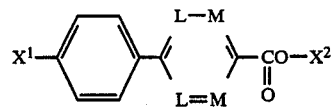

wherein $X^1$ represents an alkyl or alkoxy each of 1–10 C; $X^2$ represents a 4-substituted phenyl having an alkyl, of 1–10 C, F, Cl, Br or —CN at 4-position or a 3,4-disubstituted phenyl having f, Cl, Br or CN at 4-position and F, Cl or Br at 3-position; and either one of L or M represents =N— and the other represents —C=.

12 Claims, No Drawings

PHENYLPYRIMIDINECARBOXYLATE DERIVATIVE

This application is a continuation-in-part application of U.S. application Ser. No. 863,505, filed May 15, 1986, now abandoned.

BACKGROUND OF THE INVENTION

1. Field of the Invention

This invention relates to a novel organic compound. More particularly it relates to a compound useful as a component of liquid crystal compositions and a liquid crystal composition containing the same.

2. Description of the Prior Art

Liquid crystal display devices have been used for various display devices, by utilizing the properties of the dielectric anisotropy, optical anisotropy, etc. in the liquid crystal phases of liquid crystal compounds and/or liquid crystal compositions. These displays are of liquid crystal display elements during the electro-optic effect of liquid crystals or those employing the thermo-optic effect and other optic effects, and a number of liquid crystal compounds have been used for liquid crystal display elements using the electric field effects such as twisted nematic effect, guest-host effect, etc., in cooperation with the advance of electronics. As to these liquid crystal materials, there is no single compound which satisfies all of the various characteristics of liquid crystal elements such as mesomorphic range, operating voltage, response properties, etc.; thus, several kinds of liquid crystal compounds and if necessary, non-crystal compounds have been blended and used for practical use.

Recently, the search for a liquid crystal display element capable of being driven in a higher temperature atmosphere and/or under lower voltages have been increasing, and a liquid crystal composition having a high transition point (clearing point) of liquid crystalline phase isotropic liquid phase and/or a large dielectric anisotropy value has been desired.

The clearing point of liquid crystal composition has been known to be raised by adding a component having a high clearing point.

When liquid crystal compounds and/or liquid crystal compositions are filled in a cell provided with electrodes, and in most cases, in a cell providedc with transparent and opposed electrodes, and liquid crystal display is controlled under voltages, the following has been observed:

One of factors having an effect upon the threshold voltage ($V_{th}$) among voltages driving liquid crystal display cells in the dielectric anisotropy value $\Delta\epsilon(\Delta\epsilon = \epsilon_{\parallel} - \epsilon_{\perp})$ of liquid crystal compounds and/or liquid crystal compositions, and increase in $\Delta\epsilon$ has a tendency of reducing $V_{th}$. When $\Delta\epsilon$ is positive and large, it is possible to lower the driving voltage of cells provided with opposed electrodes having the same distance therebetween.

Some ester compounds having a pyrimidine ring have been known as liquid crystal compounds or a component of liquid crystal compositions or an intermediate thereof. As to compounds having a pyrimidine ring in the form of

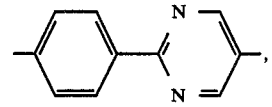

Zaschke et al disclose

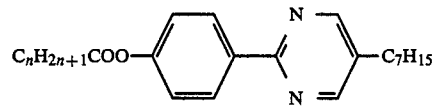

(wherein n=3–11) (Heterocyclic Liquid Crystals, Advanced Liquid Crystal Research and Applicants, Pargamon Press (1980), 1065). Further, Zaschke et al disclose

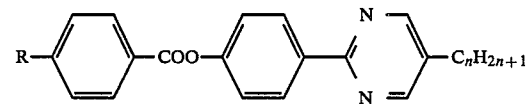

wherein R represents $C_nH_{2n+1}$, $C_nH_{2n+1}O$, $C_nH_{2n+1}OCOO$, $C_nH_{2n+1}COO$, $C_nH_{2n+1}S$, F, Cl, Br, $NO_2$, CN or $CF_3$ and n represents 1 to 10 (U.S.P. 4,311,610).

Toki et al disclose

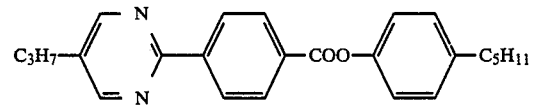

(Japanese patent application laid-open No. Sho 56-164169/1981).

Shad et al disclose a composition containing

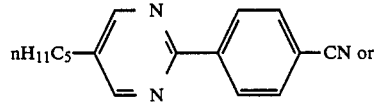

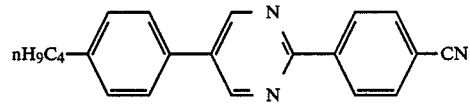

(n:mormal) on page 5, Table II in BG 2092169, but it does not concretely describe the properties of compounds wherein a phenylpyrimidinecarboxylic acid derivative and a phenyl derivative are ester-linked.

As to these compounds, the benzene ring bonded directly to the pyrimidine ring has a carbonyl group or cyano group substituent, but the above references do not disclose any compounds wherein a pyrimidine ring bonded directly to a benzene ring has a carbonyl group substituent, whereas Boller et al disclose

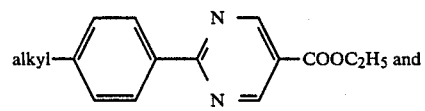

-continued

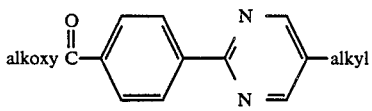

each as an intermediate of liquid crystal compounds (U.S. Pat. No. 4,062,798; Japanese patent publication No. Sho 55-27056 (1980)). However, this reference does not disclose an ester wherein the oxygen of the carboxyl group is bonded to a phenyl group.

Gray et al disclose a composition containing an ester of a 5-alkyl (or 5-alkoxy) pyrimidine-2-carboxylic acid with a 4-alkylphenol or 4-alkoxyphenol,

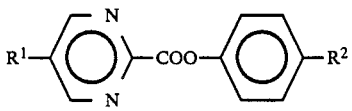

wherein each $R^1$ and $R^2$ independently represents a n-alkyl or n-alkoxy group having up to 12 carbon atoms.

And with regard to a reaction according to which a substituted-phenyl-2-(4-substituted-phenyl)-5-pyrimidine carboxylate or a substituted phenyl-5-(4-substituted phenyl)-2-pyrimidine carboxylate can be esterified, it states that methods of attachment of radicals $R_1(A)_n$ to pyrimidine rings are known and such methods may be employed in the course of the formation of the apropriate esters or their precursors $R_1(A)_n$—B-CO·OH and $R_1(A)_1$—BOH (WO 86/00067, page 14, lines 17–20).

However, Gray et al do not disclose any compounds wherein a pyrimidine ring having a carbonyl group substituent is bonded directly to a benzene ring (page 18, Table 5).

SUMMARY OF THE INVENTION

An object of the present invention is to provide a compound useful as a constituent component of liquid crystal compositions and a liquid crystal composition containing the same. Another object of the present invention is to provide a compound which, when used as a constituent component of liquid crystal compositions, can raise the clearing point of the lquid crystal compositions and/or increase Δε thereof.

(1) The present invention in a first aspect resides in a phenylpyrimidinecarboxylate derivative expressed by the general formula

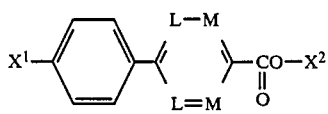

wherein $X^1$ represents an alkyl group or an alkoxy group each of 1 to 10 carbon atoms; $X^2$ represents a 4-substituted phenyl group having an alkyl group of 1 to 10 carbon atoms, F, Cl, Br or cyano group at the 4-position or a 3,4-disubstituted phenyl group having F, Cl, Br or cyano group at the 4-position and F, Cl or Br at the 3-position; and either one of L or M reprsents =N— and the other represents —C=.

(2) The present invention in a second aspect resides in a liquid crystal composition having at least two components one of which is a phenylpyrimidine derivative as set forth in the above-described paragraph (1).

DETAILED DESCRIPTION OF PREFERRED EMBODIMENTS

In the formula

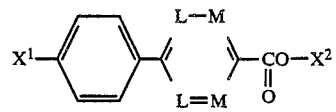

of the present invention, examples of

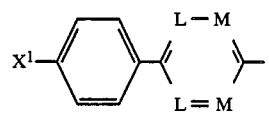

are

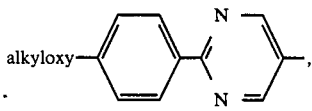

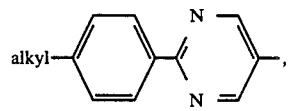

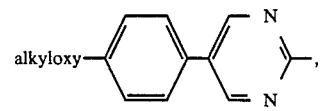

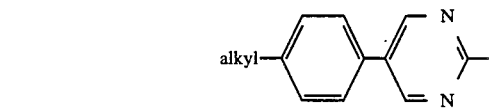

and examples of —$X^2$ are

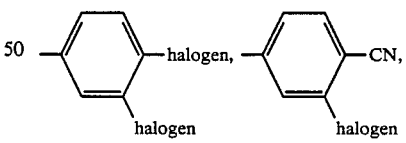

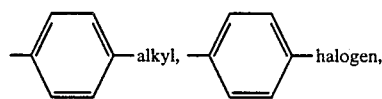

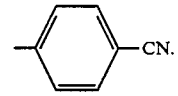

Next, preparation of a phenyl-5-pyrimidinecarboxylate derivative and that of a phenyl-2-pyrimidinecarboxylate derivative are shown below by way of Formula Scheme I and Formula Scheme II.

Formula Scheme I
(Phenyl-5-pyrimidinecarboxylate derivative)
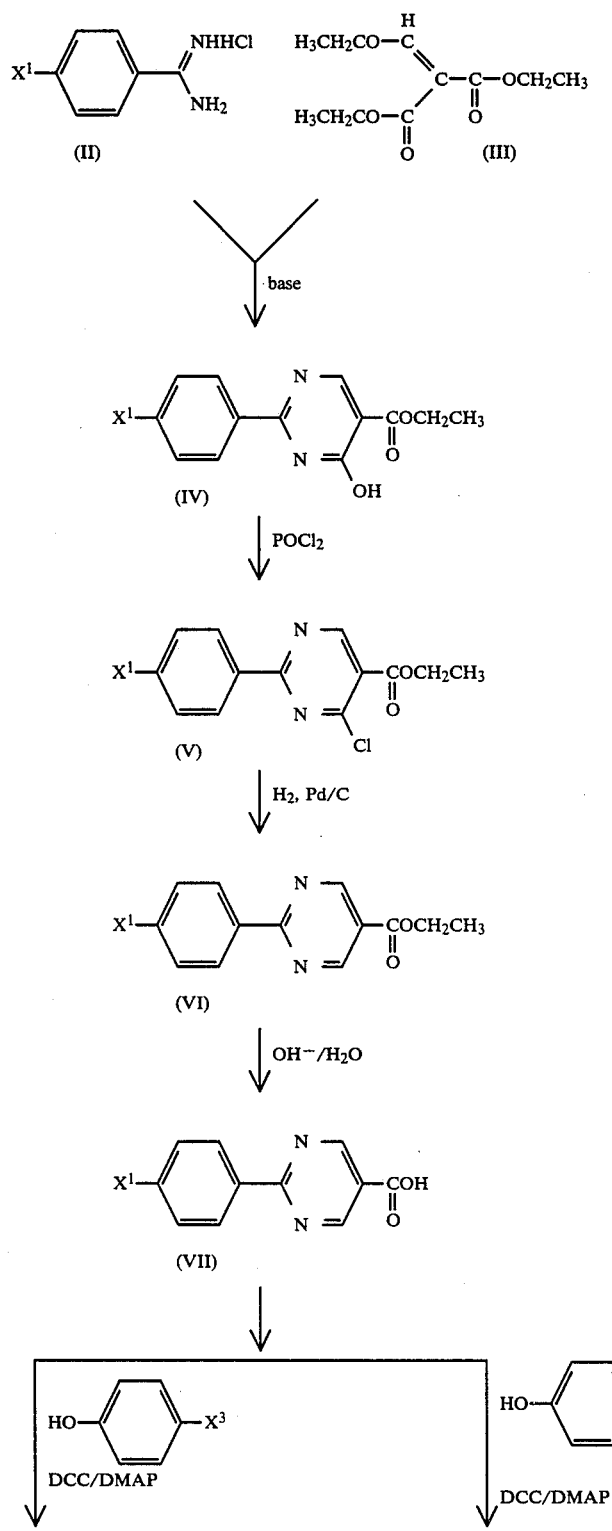

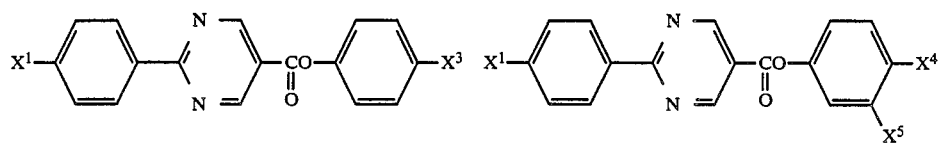
In this scheme I,
$X^1$: alkyl group or alkoxyl group
DCC: N,N'—dicyclohexyl-carboxyimide
DMAP: 4-dimethylamino-pyridine
$X^3$: alkyl group, F, Cl, Br or CN
$X^4$: F, Cl, Br or CN
$X^5$: F, Cl or Br
Formula Scheme II
(Phenyl-2-pyrimidinecarboxylate derivative)
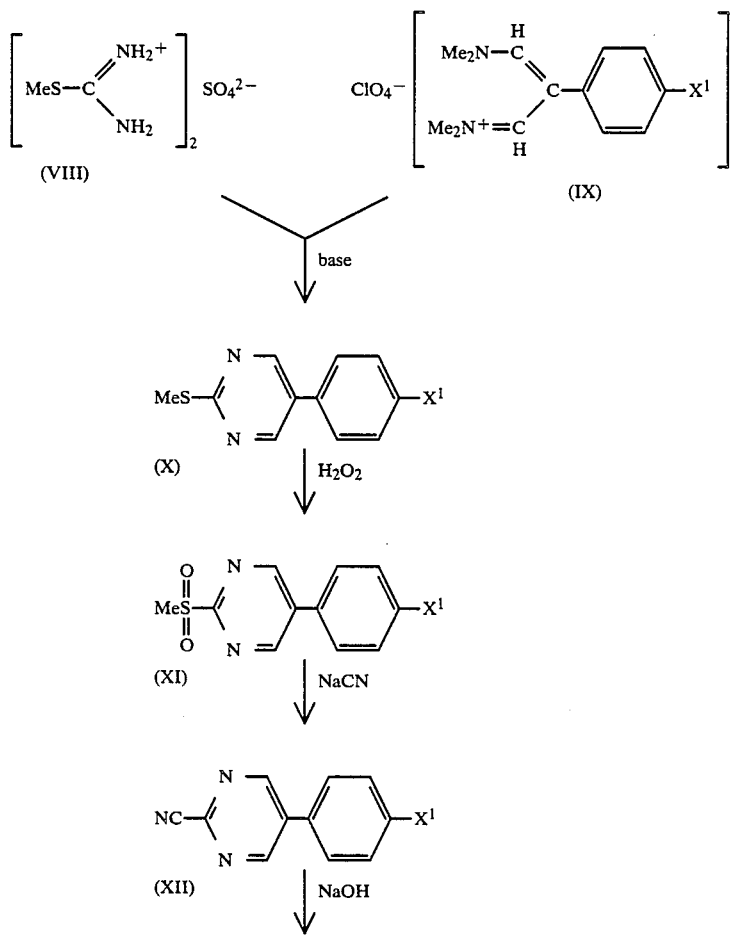

-continued
Formula Scheme II
(Phenyl-2-pyrimidinecarboxylate derivative)

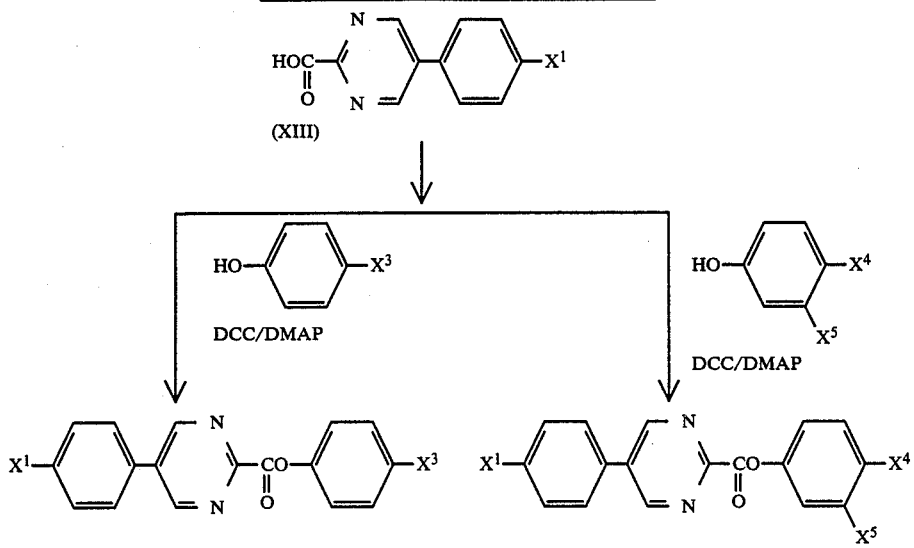

The above two preparations will be described more explicitly.

① Case of 5-pyrimidinecarboxylate:

a 4-substituted-benazmidine salt (II) and diethyl ethoxymethylenemalonate (III) are subjected to a condensation reaction to obtain a pyrimidine compound, i.e. an ethyl-2-(4'-substituted phenyl)-4-hydroxy-5-pyrimidinecarboxylate (IV). Examples of the catalyst used in the condensation reaction are bases such as metal alcoholates, KOH, 1,8-diazabicyclo[5,4,0]-7-undecene, triethylamine, etc. Next, the hydroxyl group at the 4-position of the pyrimidine ring of the above compound (IV) is chlorinated to obtain an ethyl-2-(4-sbustituted phenyl)-4-chloro-5-pyrimidinecarboxylate (V), followed by dechlorinating the compound (V) at the 4-position of the pyrimidine ring with Pd/C catalyst and hydrogen to obtain an ethyl-2-(4-substituted phenyl)-5-pyrimidinecarboxylate (VI), hydrolyzing this compound (VI) to obtain an ethyl-2-(4-substituted phenyl)-5-pyrimidinecarboxylic acid (VII).

When the compound (VII) and the above hydroxyl group-containing compound (a compound expressed by the above chemical formula

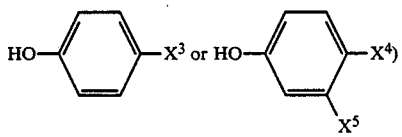

are subjected to dehydrationcondensation using 4-dimethylaminopyridine, N,N'-dicyclohexylcarbodiimide or the like, it is possible to obtain a phenyl-5-pyrimidinecarboxylate derivative.

② Case of 2-pyrimidinecarboxylate:

a methylisothiourea compound (VIII) and a perchlorate salt (IX) are subjected to a cyclization reaction in the presence of a base such as sodium methoxide, pyridine, NaOH, etc., to obtain a pyrimidine compound (X), followed by oxidizing the methylthio group fo the compound with hydrogen peroxide to obtain a compound (XI) having a methanesulfonyl group converted from the above group, reacting this compound (XI) with NaCN to obtain a 2-cyanopyrimidine derivative (XII), hydrolyzing this (XII) with a NaOH aqueous solution to obtain a 2-pyrimidine carboxylic acid derivative (XIII), and subjecting the compound (XIII) and a hydroxyl group-containing compound (a compound expressed by

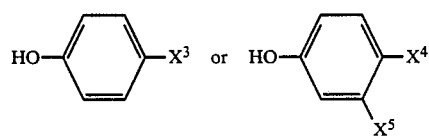

in the above chemical formulas) to dehydration-condensation by means of 4-dimethylaminopyridine, N,N-dicyclo-hexylcarbodiimide or the like, to obtain a phenyl-2-pyrimidinecarboxylate derivative.

Examples of

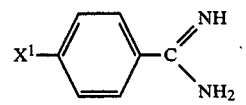

are 4-methylbenzamidine, 4-ethylbenzamidine, 4-propyl-benzamidine, 4-butylbenzamidine, 4-p[entylbenzamidine, 4-hexylbenzamidine, 4-heptylbenzamidine, 4-octylbenzamidine, 4-nonylbenzamidine, 4-decylbenzamidine, 4-methoxybenzamidine, 4-ethoxybenzamidine, 4-propyloxybenzamidine, 4-butyloxybenzamidine, 4-pentyloxybenzamidine, 4-hexyloxybenzamidine, 4-heptyloxybenzamidine, 4-octyloxybenzamidine, 4-nonyloxybenzamidine, 4-decyloxybenzamidine, etc.

Examples of the linear chanin alkyl group among alkyl groups in the above general formula and preparation schemes are ethyl, propyl, butyl, pentyl, hexyl, heptyl, octyl, nonyl and decyl, and examples of the branched chain alkyl group are isopropyl, 1-methylpropyl, 2-methylpropyl, 1-methylbutyl, 2-methylbutyl, 3-methylbutyl, 1-methylpentyl, 1-ethylpentyl, 2-methylpentyl, 1-methylhexyl, 2-ethylhexyl, 1-methylheptyl, etc.

Examples of the linear chain alkyloxy group among the alkyloxy groups as $X^1$ in the compound expressed by the general formula are methoxy, ethoxy, propoxy, butoxy, pentyloxy, hexyloxy, heptyloxy, octyloxy, nonyloxy and decyloxy, and examples of the branched alkyloxy group are isopropoxy, 1-methylbutoxy, 2-methylpropoxy, etc.

Examples of

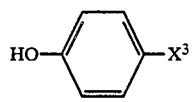

shown in the above preparation schemes are as follows:

in the case of 13 $X^3$ being a linear chain group, 4-methylphenol, 4-ethylphenol, 4-propylphenol, 4-butylphenol, 4-pentylphenol, 4-hexylphenol, 4-heptylphenol, 4-octylphenol, 4-nonylphenol and 4-decylphenol;

in the case of —$X^3$ being a branched chain group, alkylphenols having the above-mentioned branched alkyl groups at 4-position; and in the case of —$X^3$ being groups other than alkyl groups, 4-fluorophenol, 4-chlorophenol, 4-bromophenol and 4-cyanophenol.

Examples of

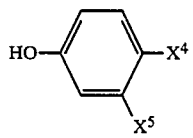

shown in the above preparation schemes are 3,4-difluorophenol, 3,4-dichlorophenol, 3,4-dibromophenol, 3-fluoro-4-chlorophenol, 3-fluoro-4-bromophenol, 3-chloro-4-fluorophenol, 3-chloro-4-bromophenol, 3-bromo-4-fluorophenol, 3-bromo-4-chlorophenol, 3-fluoro4-cyanophenol, 3-chloro-4-cyanophenol and 3-bromo-4-cyanophenol.

Examples of compounds to be blended with at least one kind of the compound of the present invention expressed by the above general formula are liquid crystal compounds of other types such as those of Schiff's base compounds, azoxy compounds, azoxybenzene compounds, ester compounds, biphenyl compounds, phenylcyclohexane compounds, phenylpyrimidine compounds, etc.

The proportion of the compound of the present invention used as the component of the liquid crystal composition may be in the range of 0.5 to 30% by weight based on the composition.

Among the compounds of the present invention, those which exhibit much of a function of raising the viscosity of the resulting liquid crystal composition may be used as a component of the liquid crystal composition in a proportion of e.g. 15% by weight or less, whereby for example, it is possible to avoid reduction in the response properties of liquid crystal display devices due to an increase in the viscosity of the liquid crystal composition at room temperature.

Examples of existing liquid crystal compounds with which the compound of the present invention can be used to give the liquid crystal composition of the present invention are expressed by the following general formulae (i) to (xxxiii):

In these formulae, Y represents

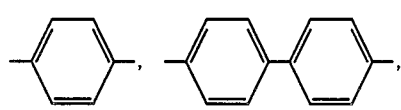

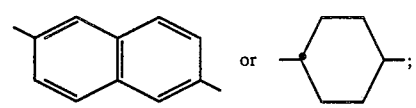

Z represents —CN, alkyl group, halo, or —COO-Z'; Z' represents —CN, alkyl group or —O—alkyl group, and R represnets an alkyl group, generally a $C_1$ to $C_{10}$ group, preferably a $C_3$ to $C_7$ group.

Furthermore, usable compounds also include those wherein one hydrogen atom in the benzene ring(s) of such compounds is substituted by a halogen atom such as F, Cl or Br.

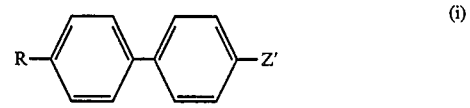 (i)

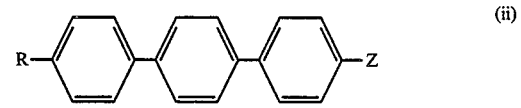 (ii)

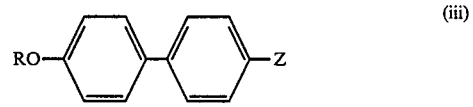 (iii)

 (iv)

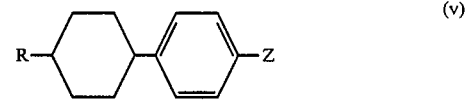 (v)

 (vi)

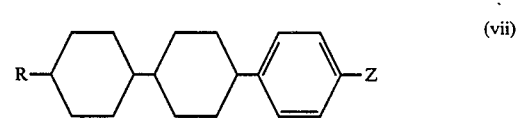 (vii)

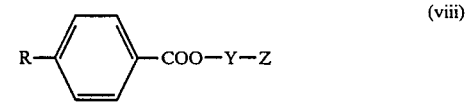 (viii)

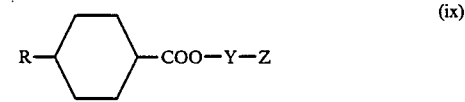 (ix)

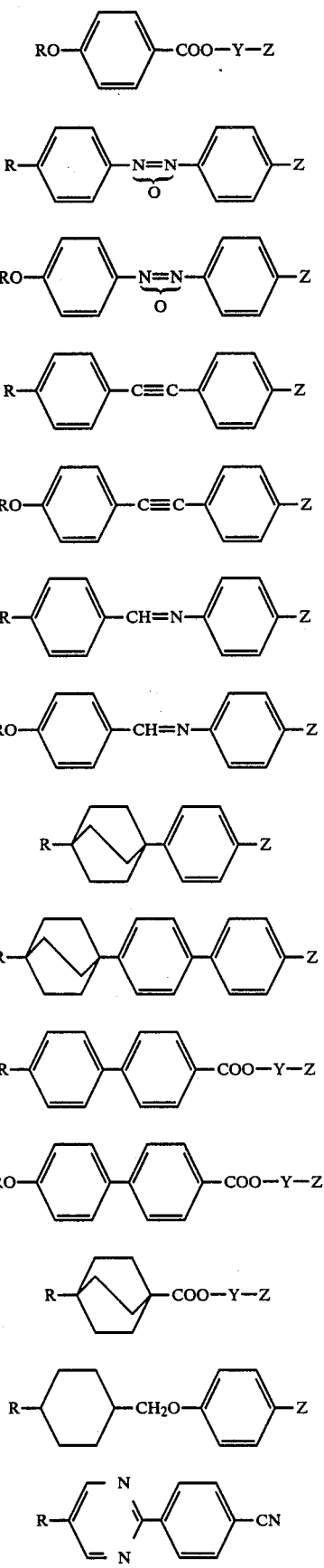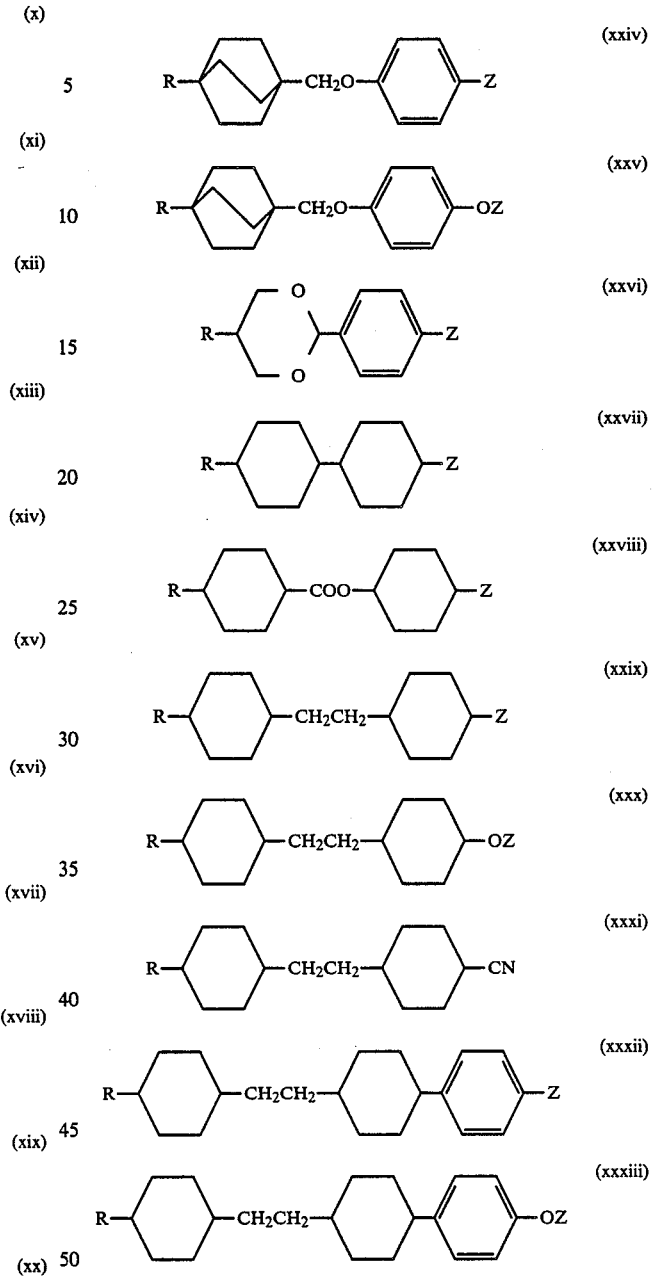

When the compound of the present invention is used as a component of liquid crystal compositions, it is possible to raise the clearing point of the mesomorphic range of the liquid crystal compositions, and/or it is possible to increase the dielectric anisotropy value of the liquid crystal compositions. For example, 3-halogeno4-halogenophenyl-2-(4-alkyloxyphenyl)-5-pyrimidinecarboxylates have a large function of broadening the clearing point of liquid crystal compositions toward the higher temperature side as comapred with the proportion by quantity thereof used as a component of the liquid crystal compositions. The compound of the present invention has a good stability to heat, light, electricity, air, moisture, etc. By using the compound of the present invention, it is possible to broaden the range in which the components of liquid crystal compositions can be chosen.

The present invention will be described in more detail by way of Examples, but it should not be construed to be limited thereto.

EXAMPLE 1

3-Chloro-4-fluorophenyl-2-(4-butyloxyphenyl)-5-pyrimidinecarboxylate (1) Ethyl-2-(4-butyloxyphenyl-5-pyrimidinecarboxylate (compound VI)

4-Butyloxybenzamidine hydrochloride (II) (22.9 g, 0.1 mol) and diethyl ethoxymethylenemalonate (III) (23.8 g, 0.1 mol) were suspended in methanol (100 ml), followed by agitating the suspension while keeping it at 10° C., dropwise adding a sodium methoxide-methanol solution, separately prepared by reacting sodium (2.5 g, 0.11 mol) with methanol (200 ml), then agitating the mixture for 2.5 hours, distilling off methanol under reduced pressure, gradually adding 6N-hydrochloric acid till the solution reached a pH of 4, filtering the resulting white precipitate, washing the precipitate with a small quantity of methanol and drying the precipitate to obtain ethyl-2-(4-butyloxyphenyl)-4-hydroxy-5-pyrimidinecarboxylate (IV) 21.9 g) (yield: 69% based on compound (II)).

Phosphorus oxychloride (61.3 g, 0.4 mol) was added to compound (IV) (15.8 g, 0.05 mol), followed by heating the mixture under reflux for 5 hours, distilling off phosphorus oxychloride under reduced pressure, adding ice water (50 g) to the residue, filtering to obtain yellow-earth color solids (20.6 g), placing the solids in a mixed solution of diethyl ether (100 ml) and 1M-$K_2CO_3$ aqueous solution, agitating the mixture, filtering off insolubles, separating an aqueous phase from the filtrate, drying the resulting fluid over anhydrous magnesium sulfate, filtering off magnesium sulfate, distilling off ether to obtain pale yellow crystals, and recrystallizing the crystals from methanol to obtain fluffy crystals of ethyl-2-(4-butyloxyphenyl)-4-chloro-5-pyrimidinecarboxylate (V) (8.6 g, 0.026 mol) (yield: 52%) having a melting point of 79.0° C.

This compound (V) (3.3 g, 10 mmols) was dissolved in ethyl acetate (30 ml), followed by agitating the solution together with Pd/C (5%) (0.6 g) and triethylamine (1.0 g) in hydrogen atmosphere at room temperature for 3 hours, filtering off Pd/C, adding toluene (100 ml), washing the resulting fluid with 2N-hydrochloric acid (50 ml), washing it with water till the washing water became pH 7, drying the toluene phase over anhydrous magnesium sulfate, filtering off magnesium sulfate, concentrating under reduced pressure to obtain white crystals and recrystallizing the crystals from methanol to obtain ethyl-2-(4-butyloxyphenyl)-5-pyrimidinecarboxylate (VI) (2.4 g) (yield: 80%) having a melting point 99.1° C.

(2) Ester interchange

NaOH aqueous solution was added to ethyl-2-(4-butyloxyphenyl)-5-pyrimidinecarboxylate (VI), followed by heating the mixture, adding hydrochloric acid, filtering off the resulting precipitates, and drying to obtain 2-(4-butyloxyphenyl)-5-pyrimidinecarboxylic acid (VII). This compound (VII) (1.0 g, 3.7 mmols), 4-dimethylaminopyridine (0.2 g), N,N'-dicyclohexylcarbodiimide (1.7 g) and 3-chloro-4-fluorophenol (0.7 g) were dissolved in dichloromethane (30 ml), followed by agitating the solution for 5 minutes, further agitating at room temperature overnight, filtering off the resulting precipitates, washing the dichloromethane phase with 2N-hydrochloric acid, then with 2N-NaOH aqueous solution and further with water till the washing water became pH 7, drying over magnesium sulfate, concentrating under reduced pressure, and recrystallizing the residual white solids from methanol to obtain the objective 3-chloro-4-fluorophenyl-2-(4-butyloxyphenyl)5-pyrimidinecarboxylate (0.5 g). This compound had a crystalline-smectic point (C-S point) of 152.3° C. and a smectic-clearing point (S-I point) of 165.4° C. The elemental analysis values of this compound were as follows: C:62.9%, H: 4.5%, N: 7.0% (calculated values in terms of $C_{21}H_{18}ClFN_2O_3$—c: 62.92%, H:4.53%, N: 6.99%).

EXAMPLE 2

4-Cyano-3-fluorophenyl-2-(4-butyloxyphenyl)-5-pyrimidinecarboxylate 2-(4-Butyloxyphenyl)-5-pyrimidinecarboxylic acid (VII) obtained by hydrolyzing ethyl-2-(4-butyloxyphenyl)-5-pyrimidinecarboxylate (VI) and 4-cyano-3-fluorophenol were subjected to dehydration-condensation in the same manner as in Example 1 to obtain the objective 4-cyano3-fluorophenyl-2-(4-butyloxyphenyl)-5-pyrimidinecarboxylate.

This compound had a crystalline-nematic point (C-N point) of 164.7° C. and a nematic-clearing point (N-I point) of 236.9° C. Its elemental analysis values were as follows: C: 67.5, H: 4.6%, N: 10.7% (calculated values in terms of $C_{22}H_{18}FN_3O_3$—C:67.51%, h:4.64%, n:10.74%).

EXAMPLE 3

4-Pentylphenyl-2-(4-butyloxyphenyl5-pyrimidinecarboxylate 2-(4-butyloxyphenyl-5-pyrimidinecarboxylic acid (VII) obtained by hydrolyzing ethyl-2-(4-butyloxyphenyl)-5-pyrimidinecarboxylate (VI) and 4-pentylphenol were subjected to dehydration-condensation in the same manner as in Example 1 to obtain 4-pentylphenyl-2-(4-butyloxyphenyl)-5-pyrimidinecarboxylate.

This compound had a C-N point of 124.8° C. and a N-I point of 195.8° C. Its elemental analysis values were as follows: C: 74.8%, H:7.2%, N: 6.7% (calculated values in terms of $C_{26}H_{30}N_2O_3$ – c: 74.79%, H: 7.24%, N: 6.71%).

EXAMPLE 4

4-Pentylphenyl-5-(4-pentyloxyphenyl)-2-pyrimidinecarboxylate

Methylisothiourea sulfate (VIII) 11.2 g, 0.04 mol) and 1-dimethylamino-3-dimethylimmonio-2-(4-pentyloxyphenyl)propene-(1)-perchlorate (IX) (10.8 g, 0.028 mol) were added to pyridine (200 ml), followed by heating the mixture to 90° C., dropwise adding a sodium methoxide-methanol solution separately prepared from sodium (1.2 g, 0.052 mol) and methanol (150 ml), heating the mixture under reflux for 2.5 hours, dissolving the reaction fluid in toluene (500 ml), washing the solution with 2N-hydrochloric acid (300 ml), then with 2N-NaOH aqueous solution (300 ml) and further with water till the washing water became neutral, drying the toluene phase over magnesium sulfate, and concentrating under reduced temperature to obtain raw crystals (7.2 g), and recrystallizing the crystals from methanol to obtain 2-methylthio-5-(4-pentyloxyphenyl)pyrimidine (X) (5.2 g). (yield: 65%). This compound (X) exhibited a C-S point of 58.8° C. and a S-I point of 65.9° C.

The compound (X) (3.0 g, 0.0105 mol) was dissolved in acetic acid (20 ml), followed by slowly dropwise adding 30% aqueous hydrogen peroxide to the solution with stirring at room temperature, filtering off the resulting crystals and recrystallizing from methanol to obtain 2-methanesulfonyl-5-(4-pentyloxyphenyl)pyrimidine (XI) (1.8 g) (yield: 55%).

This compound (XI) (1.8 g, 0.006 mol) and NaCN (0.275 g, 0.006 mol) were added to dimethylsulfoxide (5 ml), followed by mixing at 100° C. for one hour, allowing the resulting material to cool, adding water (15 ml), filtering off the resulting crystals and recrystallizing crystals from ethanol to obtain 2-cyano-5-(4-pentyloxyphenyl)pyrimidine (XII) (0.7 g) (yield: 47%) having a melting point of 100° C.

This compound (XII) (0.7 g, 0.0026 mol) was added to 2N-NaOH aqueous solution, followed by heating the mixture under reflux for 16 hours, allowing the resulting material to cool, slowly adding 2N-hydrochloric acid to make the pH of the fluid 2, filtering off the deposited precipitates to obtain yellow-earth color raw crystals, and recrystallizing the crystals from ethanol to obtain 5-(4-pentyloxyphenyl)pyrimidine-2-carboxylic acid (XIII) (0.4 g) (yield: 54%).

This compound (XIII) (0.4 g, 1.4 mmol) and 4-pentylphenol (0.4 g, 2.4 mmol) were dissolved in dichloromethane (20 ml), followed by adding 4-dimethylaminopyridine (0.2 g) and N,N'-dicyclohexylcarbodiimide (0.3 g, 1.5 mmol), mixing these at room temperature for 5 hours, filtering off the resulting urea, drying the dichloromethane solution over magnesium sulfate, distilling off dichloromethane under reduced pressure to obtain raw crystals, and recrystallizing from ethanol to obtain 4-pentylphenyl-5-(4-pentyloxyphenyl)-2pyrimidinecarboxylate (0.1 g, 0.24 mmol; yield, 17%).

This compound exhibited a C-S point of 155.1° C. and a S-I point of 185.2° C. Its elemental analysis values were as follows: C:72.1%, H:7.5% (calculated values in terms of $C_{27}H_{32}N_2O_3$ —C: 72.19%, H: 7.46%).

EXAMPLES 5 and 6

Ethyl-2-(4-propylphenyl)-5-pyrimidinecarboxylate was prepared and subjected to ester interchange in the same manner as in Example 1, whereby the following compounds were synthesized.

4-Fluorophenyl-2-(4-propylphenyl)-5-pyrimidinecarboxylate, crystalline-nematic point (C-N point) 154.4° C., nematic-clearing point (N-I point) 167.2° C.

4-Cyanophenyl-2-(4-propylphenyl)-5-pyrimidinecarboxylate, C-N point 172.0° C., N-I point 254.7° C.

All the compounds obtained by the above examples and each transition point are listed in the following Table 1.

TABLE 1

| Example | Compounds | Phase transition point (°C.) | |
|---|---|---|---|
| 1 | $C_4H_9O$-⟨phenyl⟩-⟨pyrimidine⟩-CO-O-⟨phenyl(Cl)⟩-F | C-Sm 152.3 | Sm-I 165.4 |
| 2 | $C_4H_9O$-⟨phenyl⟩-⟨pyrimidine⟩-CO-O-⟨phenyl(F)⟩-CN | C-N 164.7 | N-I 236.9 |
| 3 | $C_4H_9O$-⟨phenyl⟩-⟨pyrimidine⟩-CO-O-⟨phenyl⟩-$C_5H_{11}$ | C-N 124.8 | N-I 195.8 |
| 4 | $C_5H_{11}O$-⟨phenyl⟩-⟨pyrimidine⟩-CO-O-⟨phenyl⟩-$C_5H_{11}$ | C-Sm 155.1 156.2 | Sm-I 185.2 |
| 5 | $C_3H_7$-⟨phenyl⟩-⟨pyrimidine⟩-CO-O-⟨phenyl⟩-F | C-N 154.4 | N-I 167.2 |
| 6 | $C_3H_7$-⟨phenyl⟩-⟨pyrimidine⟩-CO-O-⟨phenyl⟩-CN | C-N 172.0 | N-I 254.7 |

Compounds 1 and 4 shown in Table 1 were enantropic and exhibited smectic A phase and compounds 2, 3, 5 and 6 therein were enantropic and exhibited nematic phase.

EXAMPLE 7

(Use example)

A liquid crystal composition (A) consisting of

C$_3$H$_7$—⟨cyclohexyl⟩—⟨phenyl⟩—CN    30 parts by weight

C$_5$H$_{11}$—⟨cyclohexyl⟩—⟨phenyl⟩—CN    40 parts by weight and

C$_7$H$_{15}$—⟨cyclohexyl⟩—⟨phenyl⟩—CN    30 parts by weight has a N-I point of 51.2° C., a dielectric anisotropy value Δε of 11.2, an optical anisotropy value Δn of 0.119 and a viscosity at 20° C. ($\eta_{20}$) of 23.4 cp.

To this liquid crystal composition (A) (98 parts by weight) was added 3-chloro-4-fluorophenyl-2-(4-pentyloxyphenyl)-5-pyrimidinecarboxylate (2 parts by weight). The resulting liquid crystal composition had a N-I point of 72.3° C., a Δε of 12.5, a $\eta$n of 0.118 and a n$_{20}$ of 27.7 cp.

Properties of liquid crystal compositions obtained by adding other compounds of the present invention to the above liquid crystal composition (A) are shown in Table 2.

EXAMPLE 8

A liquid crystal composition (B) consisting of

C$_3$H$_7$—⟨phenyl⟩—⟨phenyl⟩—CN    24 parts by weight

C$_5$H$_{11}$—⟨cyclohexyl⟩—⟨phenyl⟩—CN    36 parts by weight

C$_7$H$_{15}$—⟨cyclohexyl⟩—⟨phenyl⟩—CN    25 parts by weight and

C$_5$H$_{11}$—⟨cyclohexyl⟩—⟨phenyl⟩—⟨phenyl⟩—CN    15 parts by weight has a N-I point of 72.0, a dielectric anisotropy value Δε of 11.6, an optical anisotropy value Δn of 0.140 and a viscosity at 20° C. ($\eta_{20}$) of 27.8 cp.

To this liquid crystal composition (B) (98 parts by weight) was added 3-chloro-4-fluorophenyl-2-(4-pentyloxyphenyl)-5-pyrimidinecarboxylate (2 parts by weight). The resulting liquid crystal composition had a N-I point of 72.3° C., a Δε of 12.6, a Δn of 0.142 and a $\eta_{20}$ of 27.7 cp.

Properties of liquid crystal compositions obtained by adding the compounds of the present invention to the above liquid crystal composition (B) are shown in Table 2.

TABLE 2

| Liquid crystal composition and added component | (added % by weight) | Phase transition point (C-N point) [°C] | Phase transition point (N-I point) [°C] | Δε | Δn | Viscosity (20° C.) [c.p.] | Operation voltage Vth[V] | Operation voltage Vsat[V] |
|---|---|---|---|---|---|---|---|---|
| Liquid crystal composition (A) | | ←—— −20 (1 day+*) | 52.1 | 11.2 | 0.119 | 23.4 | 1.54 | 2.13 |
| Liquid crystal composition (A) + C4H9O–[structure with F, Cl] | (2) | ←—— −20 (1 day+*) | 52.7 | 12.5 | 0.118 | 22.9 | 1.50 | 2.13 |
| Liquid crystal composition (B) | | ←—— −20 (1 day+*) | 72.0 | 11.6 | 0.140 | 27.8 | 1.75 | 2.40 |
| Liquid crystal composition (B) + C4H9O–[structure with F, Cl] | (2) | ←—— −20 (1 day+*) | 72.3 | 12.6 | 0.142 | 27.7 | 1.68 | 2.24 |
| Liquid crystal composition (A) + C4H9O–[structure with C5H11] | (10) | ←—— −20 (1 day+*) | 62.8 | 12.1 | 0.130 | 24.5 | 1.53 | 2.20 |
| Liquid crystal composition (A) + C3H7–[structure with F] | (5) | ←—— −20 (1 day+*) | 55.6 | 11.4 | 0.125 | | 1.53 | 2.22 |
| Liquid crystal composition (A) + C3H7–[structure with CN] | (5) | ←—— −20 (1 day+*) | 57.5 | 11.6 | 0.124 | | 1.46 | 2.12 |
| Liquid crystal composition (A) + C5H11O–[structure with C5H11] | (5) | ←—— −20 (1 day+*) | 55.6 | 11.5 | 0.124 | 24.7 | 1.56 | 2.13 |

*1 day+ means more than one day.

As shown in Table 2, a liquid crystal composition containing compounds of Examples 1 and 3–6 kept its melting point low and exhibited an elevated clearing point and an enhanced dielectric anisotropy. A liquid crystal composition having compounds of Examples 1 and 6 added exhibited no large increase in viscosity in the range of proportions oin which they were added. The liquid crystal composition having compounds in Examples 1 and 3–6 added brought about changes in the optical anisotropy and the threshold voltage and saturation voltage of TN cell.

What we claim si:

1. A phenylpyrimidinecarboxylate derivative expressed by the general formula

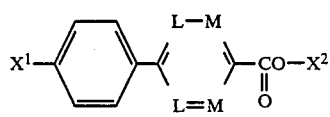

wherein $X^1$ represents an alkyl group or an alkoxy group each of 1 to 10 carbon atoms; $X^2$ represents a 4-substituted phenyl group having as a substituent an alkyl group of 1 to 10 carbon atoms and L represents =N— and M represents —C=.

2. A phenylpyrimidinecarboxylate derivative according to claim 1 wherein said derivative is a 4-alkyl-phenyl-2-(4-alkyloxyphenyl)-5-pyrimidinecarboxylate.

3. A phenylpyrimidinecarboxylate derivative according to claim 1 wherein said derivative is a 4-alkyl-phenyl-2-(4-alkylphenyl)-5-primidinecarboxylate.

4. A liquid crystal composition having at least two components one of which is a phenylpyrimidinecarboxylate derivative expressed by the general formula

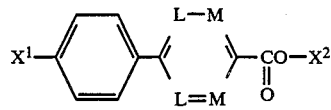

wherein $X^1$ represents an alkyl group or an alkoxy group each of 1 to 10 carbon atoms; $X^2$ represents a 4-substituted phenyl gropu having as a substituent an alkyl group of 1 to 10 carbon atoms, and L represents =N— and M represents —C=.

5. A liquid crystal composition according to claim 4 wherein said derivative is a 4-alkyl-phenyl-2-(4-alkyloxyphenyl)-5-pyrimidinecarboxylate.

6. A liquid crystal composition according to claim 4 wherien said derivative is a 4-alkyl-phenyl-2-(4-alkylphenyl)-5-pyrimidinecarboxylate.

7. A phenylpyrimidinecarboxylate derivative according to claim 2 wherein said derivative is 4-pentylphenyl-2-(4-butyloxyphenyl)-5-pyrimidinecarboxylate.

8. A liquid crystal composition according to claim 4 wherein said derivative is 4-pentylphenyl-2-(4-butyloxyphenyl)-5-pyrimidinecarboxylate.

9. A phenylpyrimidinecarboxyulate derivative according to claim 1 wherein $X^1$ represents an alkyl group or an alkoxy group each of 4 to 10 carbon atoms.

10. A phenylpyrimidinecarboxylate derivative according to claim 1 wherien the substituent in the 4-substituted phenyl group of $X^2$ is an alkyl group of 5 to 10 carbon atoms.

11. A liquid crystal composition according to claim 4 wherein $X^1$ represents an alkyl group or an alkoxy group each of 4 to 10 carbon atoms.

12. A liquid crystal composition according to claim 4 wherein the substituent in the 4-substituted phenyl group of $X^2$ is an alkyl group of 5 to 10 carbon atoms.

* * * * *